United States Patent
Ostermaier

(12) United States Patent (10) Patent No.: US 6,887,352 B2
Ostermaier (45) Date of Patent: May 3, 2005

(54) DISTILLATIVE METHOD FOR SEPARATING HEXAMETHYLENEDIAMINE FROM A MIXTURE COMPRISING HEXAMETHYLENEDIAMINE, 6-AMINOCAPRONITRILE AND TETRAHYDROAZEPINE

(75) Inventor: John J. Ostermaier, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 0 days.

(21) Appl. No.: 10/383,947

(22) Filed: Mar. 7, 2003

(65) Prior Publication Data

US 2004/0182690 A1 Sep. 23, 2004

(51) Int. Cl.[7] .............................. B01D 3/42; B01D 3/14; C07D 223/12; C07C 255/00; C07C 209/000
(52) U.S. Cl. .............................. 203/2; 203/74; 203/77; 540/605; 558/459; 564/497
(58) Field of Search ................................ 203/2, 71, 73, 203/74, 77; 564/492, 497, 456; 540/605, 612; 558/459

(56) References Cited

U.S. PATENT DOCUMENTS

| | | | | |
|---|---|---|---|---|
| 5,961,788 A | * | 10/1999 | Ostermaier | 203/37 |
| 6,139,693 A | * | 10/2000 | Bassler et al. | 203/49 |
| 6,248,926 B1 | * | 6/2001 | Ostermaier et al. | 564/492 |
| 6,300,497 B1 | | 10/2001 | Rehfinger et al. | |
| 6,346,641 B1 | | 2/2002 | Luyken et al. | |
| 6,359,178 B1 | * | 3/2002 | Fischer et al. | 564/492 |
| 6,462,220 B1 | | 10/2002 | Luyken et al. | |
| 6,599,398 B1 | * | 7/2003 | Ostermaier et al. | 203/74 |

* cited by examiner

Primary Examiner—Virginia Manoharan

(57) ABSTRACT

A method for recovering hexamethylene diamine (HMD) from a mixture comprising HMD, 6-aminocapronitrile (ACN) tetrahydroazepine (THA), and adiponitrile (ADN) is disclosed.

Figure 1:
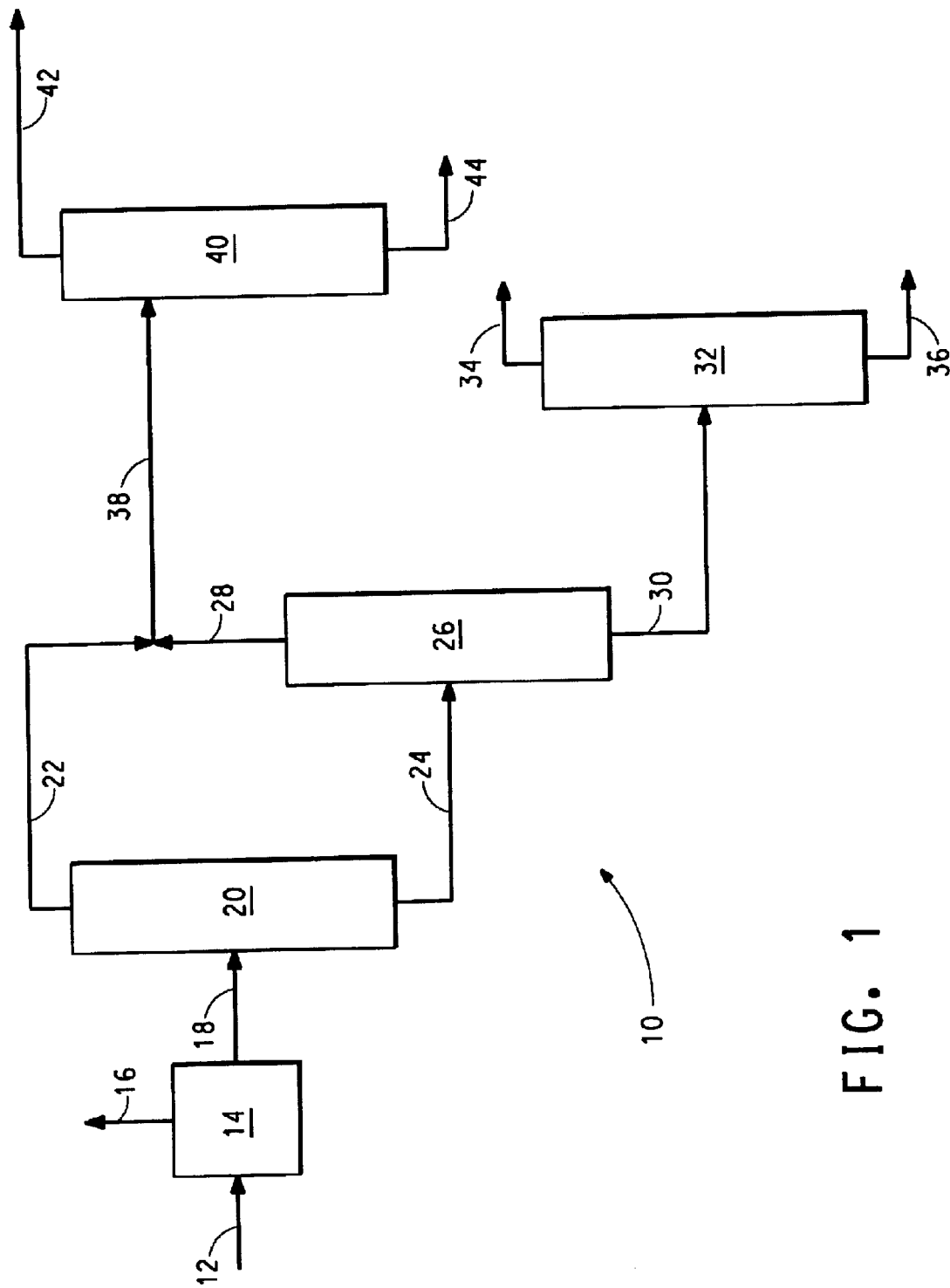

The method includes introducing the mixture into a first distillation column, separating as a group the HMD, ACN and at least a portion of the THA as distillate from the ADN. The first distillation column is operated at a temperature and pressure to minimize isomerization of the ADN into 2-cyanocyclopentylideneimine(CPI). The distillate of the first distillation column is introduced into a subsequent distillation column and the HMD is separated from the ACN and THA.

8 Claims, 1 Drawing Sheet

DISTILLATIVE METHOD FOR SEPARATING HEXAMETHYLENEDIAMINE FROM A MIXTURE COMPRISING HEXAMETHYLENEDIAMINE, 6-AMINOCAPRONITRILE AND TETRAHYDROAZEPINE

BACKGROUND OF THE INVENTION

It is well known in the Nylon industry that adiponitrile (ADN) can be hydrogenated catalytically to produce hexamethylenediamine (HMD) by complete hydrogenation, or mixtures of 6-aminocapronitrile (ACN) and HMD by partial hydrogenation. The hydrogenation reaction product also contains unreacted ADN and unwanted byproducts such as tetrahydroazepine (THA). After hydrogenation, the reaction product must be refined, generally by methods involving fractional distillation, and HMD and ACN must be separated from each other.

It is also known that if the refining conditions involve too high a temperature, the unreacted ADN can isomerize into CPI (2-cyanocyclopentylideneimine). The CPI generally distills with the ADN, and if the CPI/ADN mixture is recycled back to the hydrogenation reactor, the CPI can form AMC (2-aminomethylcyclopentylamine), which, if unseparated from the HMD, can cause inferior Nylon 6,6 to be made.

A solution to the problem is disclosed in U.S. Pat. Nos. 6,346,641 and 6,462,220 that teach distillation processes in which the column temperatures are kept below 185 deg C. However, none of these patents teach methods which allow distillation to be performed in a manner in which HMD can be recovered substantially free of THA.

U.S. Pat. No. 6,300,497 B1 teaches a method for reducing the THA content of a THA/HMD mixture by distillation using column head pressures between 0.3 and 3.0 bar, as well as reducing the THA content of a THA/ACN mixture by distillation using column head pressures between 0.1 and 1.3 bar. U.S. patent application Ser. No. 2003/0023083 A1 teaches a method for reducing the THA content of a THA/HMD mixture by distillation using column head pressures between 0.001 and 0.3 bar, as well as reducing the THA content of a THA/ACN mixture by distillation using column head pressures between 0.001 and 0.2 bar. However, neither of these teach a method in which a three component ACN/HMD/THA mixture is distilled so that the ACN and the HMD can be separated from one another in such a way that a substantial portion of the THA remains with the ACN, particularly when the three component ACN/HMD/THA mixture is one that is derived from the product that is produced by the partial hydrogenation of ADN, such a product containing unreacted ADN, that is capable of being isomerized into undesirable CPI if distillation temperatures in the refining train exceed about 195 deg C.

SUMMARY OF THE INVENTION

In accordance with the present invention, the ADN hydrogenation reaction product is distilled in a way that ADN is separated from ACN and HMD as early as possible so that subsequent distillative separations can be performed at temperatures above 195 deg C. It has been found that distillation of ACN, HMD and THA mixtures at column head pressures and column pressure drops that cause column temperatures to exceed 195 deg C. drives THA into the bottoms and allows substantially THA-free HMD to be recovered as a distillate.

The present invention is, therefore, a method for recovering hexamethylenediamine (HMD) from a mixture comprising HMD, 6-aminocapronitrile (ACN) tetrahydroazepine (THA), and ADN comprising:

(a) introducing the mixture into a distillation column capable of separating as a group the HMD, ACN and at least a portion of the THA from the ADN, while minimizing the isomerization of the ADN into CPI; and (b) introducing the HMD, ACN and at least a portion of the THA into a distillation column capable of separating the HMD from the ACN in such a way that the THA separates along with the ACN a method for separating hexamethylenediamine (HMD) from a mixture comprising HMD, 6-aminocapronitrile (ACN) and tetrahydroazepine (THA).

Preferably step (b) is accomplished by a method comprising:

introducing the HMD, ACN and at least a portion of the THA into a distillation column having a head pressure of at least 200 mm Hg and a pressure drop across the column of greater than 25 mm Hg, withdrawing a distillate comprising HMD and at most a minor portion of the THA, and withdrawing a bottoms comprising ACN and a major portion of the THA.

DETAILED DESCRIPTION OF THE INVENTION

Referring now to FIG. 1, there is shown distillation apparatus 10 that incorporates the process of the present invention.

A feed stream 12 containing ammonia, HMI (hexamethyleneimine), HMD, THA, ACN, ADN, and HB (high boilers) is fed into an ammonia flasher 14 in which ammonia 16 is separated from the feed stream 12. The ammonia flasher 14 preferably is one that operates at atmospheric pressure. An ammonia-depleted feed stream 18 exiting the ammonia flasher 14 is fed into a first distillation column 20 in which HMI, HMD, ACN, and THA are removed as a distillate 22 and ADN, a minor portion of the ACN in the feed stream, and HB (high boilers) are removed as a bottoms 24. Preferably column 20 is a vacuum distillation column that contains structured packing (not shown) and operates at about 60 mm Hg head pressure. The use of 60 mm Hg head pressure avoids the need for columns having excessively large column diameters. The bottoms withdrawal rate is adjusted to maintain a bottoms 24 temperature below about 195 deg C. It is important to maintain a bottoms 24 temperature below about 195 deg C. in order to avoid isomerizing ADN into CPI. The bottoms 24 are fed into a second distillation column 26 in which ACN and a minor portion of HMD are removed as distillate 28 and the major portion of ADN and HB are removed as bottoms 30. Distillation column 26 preferably is a vacuum distillation column containing structured packing (not shown) and operating at a head pressure of about 20 mm Hg. The use of a head pressure of only 20 mm Hg allows the efficient separation of ACN from ADN without causing undesirable high temperatures of the bottoms 30, which could result in the formation of CPI. The bottoms 30 from the second distillation column 26 are fed into a third distillation column 32 in which ADN is removed as distillate 34 and HB (and a minor portion of ADN) is removed as bottoms 36. Distillation column 32 is a vacuum distillation column having structure packing (not shown) and operating at a head pressure of about 20 mm Hg. Head pressures of higher than 20 mm Hg would be expected to cause unwanted CPI formation. The distillate 28 from the second distillation column 26 is combined with the distillate from the first distillation column 20 to form a feed stream 38 that is fed into a fourth distillation column 40 in which the head pressure is at least 200 mm Hg and in which there is a column pressure drop of at least 25 mm Hg. Under these conditions, HMI, HMD and at most a minor portion of THA are removed as distillate 42 and ACN and the major portion of THA are removed as bottoms 44. The fourth distillation column is a vacuum distillation column containing structured packing, so-called dump packing or trays. The internal structure of the column is not critical. Operating column 40 at head pressures above about 200 mm Hg allows THA to be preferentially removed as bottoms along with ACN, providing a distillate 42 having greatly reduced amounts of THA.

EXAMPLE

This example illustrates the invention as claimed herein and is not intended to be limiting.

Feed

The feed contained 1000 ppm THA, 39.3% HMD, 35.5% ACN, 24.4% ADN, but contained no CPI.

Equipment

Distillation column 20 was 2 inches in diameter, vacuum jacketed, and consisted of 15 feet of Sulzer® BX packing, with feed to a reboiler. Distillation column 40 was the same as column 20, except that an additional 10 feet of packing was added to the column to give 10 feet of stripping and 15 feet of rectification.

Analytical

Samples taken from the distillation columns were analyzed by gas chromatography. Compositions were determined by area % (no internal standards were used).

Distillation Column 20 Operation

The purpose of this column is to take most of the HMD, low boilers, and ACN overhead, and obtain a bottoms stream that contains the ADN and high boilers, as well as some ACN. The column feed is into the reboiler to maintain a reduced reboiler temperature and minimize CPI generation. The bottoms to feed flow ratio was varied to give two operating states, where the bottoms temperature was controlled at 185 and 190 deg C. This was done to see the effect of bottoms temperature on ACN recovery and CPI generation.

The column configuration consisted of 15 feet of Sulzer® BX packing above the reboiler. There was a reflux splitter at the top of the column, followed by a heated water condenser, followed in turn by a cold-water condenser to remove any low boilers (water) that might pass through the heated condenser. The feed was preheated to 100 deg C. with atmospheric steam.

The column was operated at 60 mm Hg head pressure, and the total column pressure drop was 25 mm Hg. Reflux ratio was set at about 1. The reboiler temperature was varied by changing the ratio of the feed rate to the bottoms flow rate.

Column 20 operating data for the two states are as follows:

|  | State 1 | State 2 |
|---|---|---|
| Head Pressure | 60 mm Hg | 60 mm Hg |
| Column delta P | 25 mm Hg | 25 mm Hg |
| T at top | 127 deg C. | 25 deg C. |
| T at 5' below top | 147 deg C. | 147 deg C. |
| T at 10' below top | 148 deg C. | 148 deg C. |
| T at bottoms | 185 deg C. | 190 deg C. |

Analysis of the distillate and bottoms streams associated with the two operating states are shown below:

|  | State 1 | State 2 |
|---|---|---|
| Distillate | | |
| ppm THA | 2100 | 3400 |
| % HMD | 55.5 | 54.0 |
| % ACN | 43.5 | 43 |
| % ADN | ND | ND |
| Bottoms | | |
| ppm THA | 500 | 340 |
| % HMD | 2.0 | 1.7 |
| % ACN | 14.0 | 9.0 |
| % ADN | 82 | 87 |
| % CPI | 55 | 170 |

ND = not detectable

Distillation Column 40 Operation

Distillation column 40 takes the Distillation column 20 distillate and separates it into HMD distillate with less than 0.1% ACN, and a bottoms stream which contains less than 100 ppm HMD. This column must also be able to remove the THA from the distillate and force most of it, if not all, into the bottoms stream. This example shows that the THA content of the distillate can be reduced by operating at increased pressure.

The column configuration consisted of 10 feet of packing below the feed point, and 15 feet of packing above the feed point. The feed was preheated to 100 deg C., and the reflux ratio was approximately 2.0.

The distillate contained 0.25% ACN, and the bottoms less than 100 ppm of HMD at all pressures. The THA content of the HMD distillate varied with column pressure as follows:

| Pressure (mm Hg) | 100 | 200 | 400 |
|---|---|---|---|
| THA in distillate (ppm) | 650 | 300 | 60 |

This example shows that if ADN is removed early in the refining train, the amount of CPI that is generated in the refining train can be kept within tolerable limits. The example further shows that by removing ADN early in the refining train, subsequent column operations can be operated above temperatures of about 185 deg C., and this in turn provides flexibility regarding column head pressures, that, in turn, allows sufficiently high head pressures to be used in Distillation column 40 so that a substantially amount of THA can be forced into the bottoms along with the ACN and that HMD, relatively free of THA, can be recovered as distillate.

What is claimed is:

1. A method for recovering hexamethylene diamine (HMD) from a mixture comprising HMD, 6-aminocapronitrile (ACN), tetrahydroazepine (THA), and adiponitrile (ADN) comprising:

introducing the mixture into a first distillation column;

separating as a group the HMD, ACN and at least a portion of the THA from the ADN, wherein the HMD, ACN and at least a portion of the THA is removed as distillate and wherein the first distillation column in operated at a temperature and pressure to minimize isomerization of the ADN into 2-cyanocyclopentylideneimine (CPI);

introducing a composition comprising the distillate of the first distillation column into a subsequent distillation column; and separating the HMD from the ACN and THA, wherein the distillate from the subsequent distillation column comprises HMD and the bottoms from the subsequent distillation column comprises the ACN and THA.

2. The method of claim 1 wherein the subsequent distillation column has a head pressure of at least 200mm Hg and a pressure drop across the column of greater than 25 mm Hg.

3. The method of claim 2 wherein the distillate of the subsequent distillation column comprises HMD and a minor portion of the THA introduced to the subsequent distillation column.

4. The method of claim 3 wherein a bottoms from the subsequent distillation column, comprising ACN and a major portion of the THA introduced to the subsequent distillation column is removed from the subsequent distillation column.

5. The method of claim 1 wherein the subsequent distillation column is operated at a temperature greater than 195° C.

6. The method of claim 1 wherein the first distillation column is operated at a head pressure of about 60 mm Hg.

7. The method of claim 1 wherein the first distillation column is operated at a temperature less than 195° C.

8. A method for recovering hexamethylene diamine (HMD) from a mixture comprising HMD, 6-aminocapronitrile (ACN), tetrahydroazepine (THA), and adiponitrile (ADN) comprising:

introducing the mixture into a first distillation column, separating the mixture in the first distillation column to remove a bottoms comprising ADN and a distillate comprising HMD, ACN and at least a portion of the THA, wherein the first distillation column is maintained at a temperature and pressure to minimize isomerization of the ADN to 2-cyanocyclopentylideneimine (CPI);

introducing a composition comprising the distillate of the first distillation column into a subsequent distillation column; and separating the composition comprising the distillate of the first distillation column in the subsequent distillation column, wherein the subsequent distillation column is maintained at a temperature and pressure such that a distillate removed from the subsequent distillation column comprises HMD and is substantially free of THA.

* * * * *